(12) United States Patent
Black

(10) Patent No.: US 6,833,110 B2
(45) Date of Patent: Dec. 21, 2004

(54) TEST MEMBER

(75) Inventor: Murdo M. Black, Ipswich (GB)

(73) Assignee: Hypoguard Limited, Woodbridge (GB)

( * ) Notice: Subject to any disclaimer, the term of this patent is extended or adjusted under 35 U.S.C. 154(b) by 195 days.

(21) Appl. No.: 09/909,456

(22) Filed: Jul. 19, 2001

(65) Prior Publication Data

US 2002/0044890 A1 Apr. 18, 2002

Related U.S. Application Data

(60) Provisional application No. 60/220,527, filed on Jul. 24, 2000.

(30) Foreign Application Priority Data

Jul. 20, 2000 (GB) ................................................ 0017738

(51) Int. Cl.$^7$ .............................................. G01N 31/00
(52) U.S. Cl. ........................... 422/56; 422/55; 422/57; 422/58; 422/60; 422/68.1
(58) Field of Search ............................ 422/56, 55, 57, 422/58, 61, 68.1

(56) References Cited

U.S. PATENT DOCUMENTS

| 4,999,582 | A | * | 3/1991 | Parks et al. ................... 324/438 |
| 5,192,415 | A | * | 3/1993 | Yoshioka et al. ......... 204/403.08 |
| 5,288,636 | A | * | 2/1994 | Pollmann et al. ......... 204/403.14 |
| 5,354,447 | A | * | 10/1994 | Uenoyama et al. ......... 205/777.5 |
| 5,395,504 | A | * | 3/1995 | Saurer et al. ............. 204/403.03 |
| 5,695,947 | A | * | 12/1997 | Guo et al. ................... 435/11 |
| 5,885,429 | A | * | 3/1999 | Friese et al. ................. 204/427 |
| 6,071,251 | A | * | 6/2000 | Cunningham et al. ...... 600/584 |
| 6,174,420 | B1 | * | 1/2001 | Hodges et al. ......... 204/403.14 |
| 6,258,229 | B1 | * | 7/2001 | Winarta et al. ......... 204/403.04 |
| 6,299,757 | B1 | * | 10/2001 | Feldman et al. ............. 205/775 |
| 6,377,894 | B1 | * | 4/2002 | Deweese et al. .............. 702/22 |
| 6,488,827 | B1 | * | 12/2002 | Shartle ................... 204/403.01 |
| 6,540,891 | B1 | * | 4/2003 | Stewart et al. ......... 204/403.14 |
| 6,565,738 | B1 | * | 5/2003 | Henning et al. ......... 205/777.5 |
| 2002/0099308 | A1 | * | 7/2002 | Bojan et al. ................. 600/573 |

FOREIGN PATENT DOCUMENTS

| EP | 0 159 727 A | 10/1985 |
| EP | 0 474 145 A2 | 3/1992 |
| EP | 0 547 709 A2 | 6/1993 |
| EP | 0 785 433 A2 | 7/1997 |
| GB | 2 328 023 A | 2/1999 |
| WO | WO 99/13101 A1 | 3/1999 |

* cited by examiner

Primary Examiner—Yelena Gaki
Assistant Examiner—Sam P. Siefke
(74) Attorney, Agent, or Firm—Thompson Coburn LLP

(57) ABSTRACT

A test member suitable for use in a test device for testing of analyte concentration in a fluid to be applied thereto comprises a base member (2) having a working area (4) to which the fluid is to be applied, containing a reagent which is reactive to the said analyte to produce an electrical signal or a color change, and a non-working area (8) adjacent to the working area (4). The total thickness of the test member in at least a portion of the non-working area (8) is at least as great as the total thickness of the test member in the working area (4).

7 Claims, 2 Drawing Sheets

Section A - A ent No. 60/220,527, filed Jul. 24, 2000.
TEST MEMBER

This application claims the benefit of provisional application No. 60/220,527, filed Jul. 24, 2000.

BACKGROUND OF THE INVENTION

1. Field of the Invention

The present invention relates to a test member for measuring the concentration of an analyte in a fluid sample, notably to a test strip for analysing blood glucose or other analytes in bodily fluids.

2. Background of the Invention

Diabetics regularly need to test samples of their blood to determine the level of blood glucose. The results of such tests may be used to determine levels of medication needed to treat the diabetes at the time. In one known type of system, disposable sensors are used to test the blood. The sensors typically take the form of test strips which are provided with a reagent material that will react with blood glucose to produce an electrical signal. Conductive tracks on the test strip relay the electrical signal to a meter which displays the result. After a sample of blood has been applied to the test strip and the measurement has been taken, the test strip is disposed of. In order to couple the conductive tracks on a test strip with the meter, the test strip needs to be inserted into a sensor holder prior to the start of testing. The sensor holder has corresponding electrodes which are brought into electrical contact with the conductive tracks of the test strip. Alternatively, the reagent in the test strip may undergo a visible color change, the magnitude of which is used to determine the analyte concentration in the applied fluid.

It is known to provide a stack of disposable circular test elements in a cylindrical housing, the stack being urged towards a test station by a spring to form a liquid-proof seal, for example as described in WO 94/10558.

A problem with providing disposable test members in a stack is that the working area to which the fluid sample will be applied can become scuffed, particularly when a compressive force is applied to the stack by a spring.

It is an object of the present invention to provide an improved test member suitable for use in test devices that employ test members in a stack.

SUMMARY OF THE INVENTION

According to an aspect of the present invention there is provided a test member suitable for use in a test device for testing of analyte concentration in a fluid to be applied thereto, the test member comprising a base member having a working area to which the fluid is to be applied, containing a reagent which is reactive to the said analyte to produce an electrical signal or a color change, and a non-working area adjacent to the working area, wherein the total thickness of the test member in at least a portion of the non-working area is at least as great as the total thickness of the test member in the working area.

By making the non-working area at least as thick as the working area, scuffing or abrasion of the working area in a stack can be reduced. Moreover, if a compressive load is applied to a stack of the test members, this may be spread out over a greater area, thereby reducing the possibility of compressive damage to the working area.

In a preferred embodiment, at least a part of the non-working area is of greater total thickness than the thickness of the working area. This further reduces the likelihood of damage to the working area by scuffing or abrasion when in a stack. The difference in thickness is preferably from 1 to 20 μm, notably from 5 to 10 μm.

The test member may be of any desired shape for a particular application; however, typically the test member will be an elongate test strip. For convenience hereinafter, the invention will be described with reference to such a test strip. However, it is to be understood that the invention is not limited to this embodiment.

In one embodiment, the reagent is reactive to the analyte to produce a visible color change. Alternatively, the reagent may react with the analyte to produce an electrical signal which is measured and displayed by a meter. In this embodiment, the working area has electrodes which are electrically connected to electrode tracks in the non-working area, and at least part of the tracks are exposed for connection to electrodes of a meter. The invention will be described hereinafter with reference to this embodiment.

To build up the working area, a plurality of layers are sequentially applied to the base layer, for example by screen printing, typically with curing or drying steps between the application steps. The layers which are printed typically comprise electrode patterns, a reagent layer, and a mesh layer (for spreading out an applied fluid). As a result of the application of these layers, the working area of a conventional electrochemical test strip is typically about 100 μm thicker than the non-working area, which contains the electrode tracks and, typically, a dielectric layer. A stack of 100 test strips will therefore be about 10 mm thicker in the working area than in the non-working area. In a test strip in accordance with the present invention, at least a part of the non-working area may be made thicker by any suitable means. Suitable means include, for example: a printed relief ink; an applied pad or tape; embossing of the base layer or an intermediate layer; or an extension of the mesh layer from the working area.

DESCRIPTION OF THE DRAWINGS

The invention will now be further described, by way of example, with reference to the following drawings in which.

DETAILED DESCRIPTION

Figure 1:
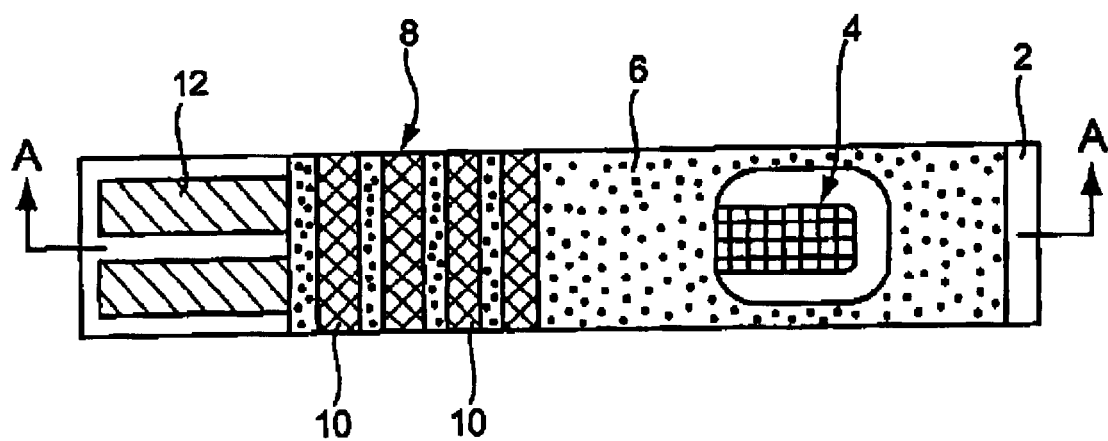
FIG. 1 is a top plan view of a test strip in accordance with the present invention.
Figure 2:
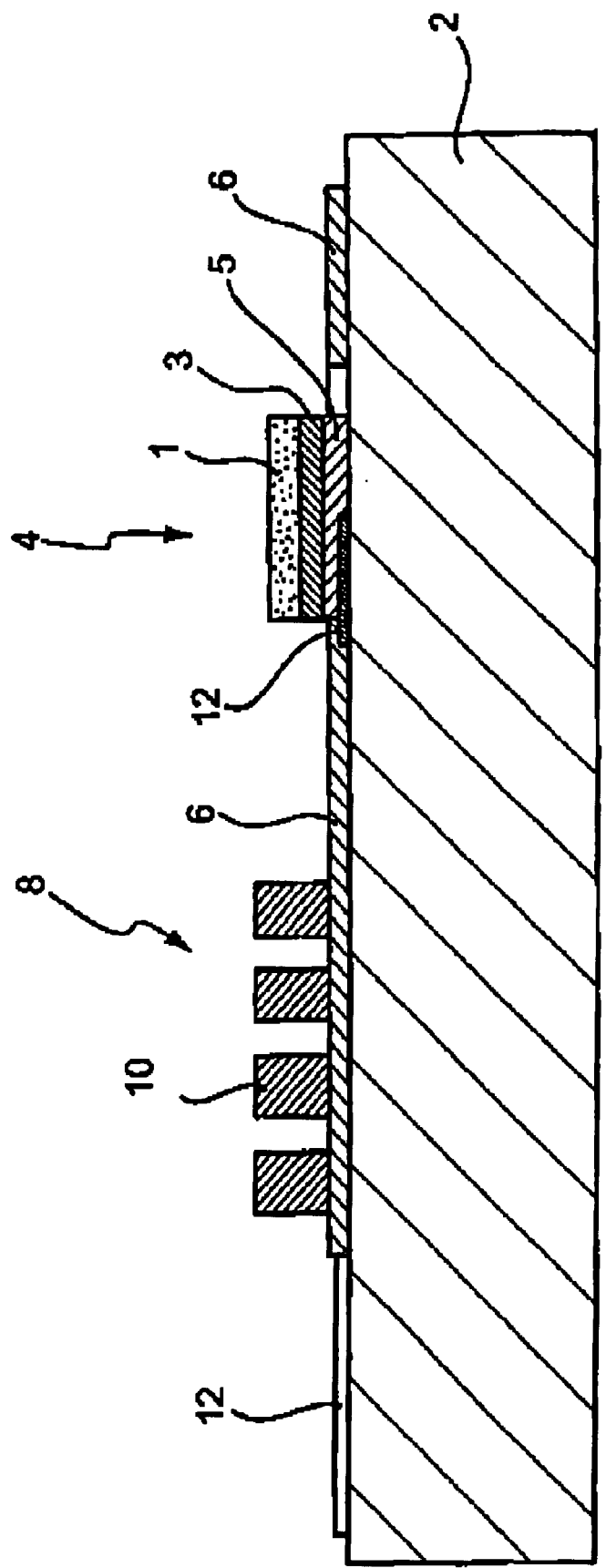
FIG. 2 is a sectional view along the line A—A of FIG. 1.

The exemplified test strip comprises a planar base member 2, in this example of poly(butylene terephthalate) (PBT) (Valox®) FR1 from GE Plastics). The strip is 30 mm×5.5 mm, and 0.5 mm thick A working area 4 of conventional construction, comprising a plurally of electrode 5, a reagent layer 3 in intimate contact with the electrodes, and a mesh layer 1 for spreading out a drop of fluid to be received on the working area. Electrode tacks 12, for example of carbon, in the non-working area 8 of the test strip are connected to the electrodes in the working area 4 in known manner. also in known manner, a die electric layer 6 is printed around the working area 4 so as to overlie a portion of the electrode tracks 12, leaving just the ends of the tracks exposed for connection to corresponding electrodes on a meter. The layers are applied to the base member as inks, by screen printing. Each ink layer is about 10 to 20 μm thick, and the mesh is about 59 to 67 μm thick. The working area 4 has a total thickness which is about 100 μm thicker than the non-working area 8 up to the dielectric layer 6.

To increase the thickness of parts of the non-working area, a high relief ink 10 has been printed in four strips. The high relief ink has a dried thickness such that the total thickness of the non-working area to which the high relief ink 10 has been applied is slightly greater than the total thickness of the test strip in the working area 4. Thus, when a stack of such test strips is formed, and a compressive load is applied to the stack by a spring, the working area 4 will not bear all the compressive load. If the test strips are used in a device which requires one strip to be slid out before being used to test analyte concentration in a fluid, scuffing of the test area will be reduced compared to a conventional test strip in which the working area stands proud of the non-working area.

Although the invention has been illustrated with reference to the use of a high relief ink printed in strips, it will be understood that it is not limited to this embodiment. The ink could be printed as a continuous block, and it could entirely surround the working area if desired. Instead of, or in addition to, the high relief ink, other means could also be provided to increase the thickness of the non-working area, for example: an applied pad or tape; embossing of the base layer or an intermediate layer; or an extension of the mesh layer from the working area into the non-working area.

What is claimed is:

1. A test member for producing an electrical signal in response to the concentration of analyte in a fluid applied thereto, the teat member comprising;

adjacent working and non-working areas that together define a top surface of the test member and together define an opposite bottom surface of the test member, the working area being adapted and configured to engage a fluid applied thereto and having a total thickness between an uppermost portion of the top surface of the test member in the working area and a lowermost portion of the bottom surface in the working area, the working area comprising a reagent and a plurality of electrodes, the non-working area having a total thickness between an uppermost portion of the top surface of the test member in the non-working area and a lowermost portion of the bottom surface of the test member, the non-working area comprising a plurality of electrode tracks and a dielectric layer, the plurality of electrode tracks being electrically connected to the electrodes of the working area of the test member, the dielectric layer overlaying a first portion of the electrode tracks, a second portion of the electrode tracks being exposed, the total thickness of the non-working area being greater than the total thickness of the working area such list, when the test member is sandwiched in a vertical stack of identical test members, the working area of the test member will not engage an identical test member positioned immediately thereabove.

2. A test member in accordance with claim 1 wherein the total thickness of the non-working area is between 1 and 20 $\mu$m greater than the total thickness of the working area.

3. A test member in accordance with claim 2 wherein the total thickness of the non-working area is between 5 and 10 $\mu$m greater than the total thickness of the working area.

4. A test member in accordance with claim 1 wherein the non-working area of the test member comprises an ink layer that contributes to the total thickness of the non-working area.

5. A test member in accordance with claim 1 wherein the test member is shaped as an elongate strip.

6. A test member in accordance with claim 1 the reagent is configured and adapted to react with glucose in blood.

7. A test member in accordance with claim 1 wherein the lowermost portion of the bottom surface of the test member is the lowermost portion of the bottom surface in the working area.

* * * * *